United States Patent [19]

Siems

[11] Patent Number: 4,528,841

[45] Date of Patent: Jul. 16, 1985

[54] APPARATUS FOR TESTING CIGARETTES AND THE LIKE

[75] Inventor: Wolfgang Siems, Hamburg, Fed. Rep. of Germany

[73] Assignee: Hauni-Werke Körber & Co. KG, Hamburg, Fed. Rep. of Germany

[21] Appl. No.: 578,359

[22] Filed: Feb. 8, 1984

[30] Foreign Application Priority Data

Feb. 16, 1983 [DE] Fed. Rep. of Germany ....... 3305235

[51] Int. Cl.³ .............................................. G01M 3/04
[52] U.S. Cl. ............................................ 73/38; 73/41; 73/49.8
[58] Field of Search ..................... 73/41, 38, 49.8, 49.2

[56] References Cited

U.S. PATENT DOCUMENTS

| | | | |
|---|---|---|---|
| 3,258,117 | 6/1966 | Domeck et al. ..................... | 73/38 X |
| 3,386,281 | 6/1968 | Menge et al. ...................... | 73/49.8 X |
| 3,948,084 | 4/1976 | Heitmann et al. ................. | 73/49.8 X |
| 3,962,906 | 6/1976 | Heitmann et al. ................. | 73/38 X |
| 4,429,567 | 2/1984 | Koch et al. ........................ | 73/49.8 |

Primary Examiner—Kenneth M. Schor

Attorney, Agent, or Firm—Peter K. Kontler

[57] ABSTRACT

Cigarettes in the peripheral flutes of a rotary drum-shaped conveyor are tested while their end portions extend into elastic tubes which are deformable radially inwardly into sealing engagement with the wrappers of the respective end portions in response to axial deformation directly by the respective end faces of the conveyor. The tubes are mounted on two ring-shaped carriers which are adjacent to the end faces of the conveyor and rotate about axes which are slightly inclined with reference to the axis of the conveyor so that each tube approaches the conveyor during one-half and moves away from the conveyor during the other half of each revolution of the conveyor and that corresponding carrier. A gaseous testing fluid is admitted into the ends of cigarettes while the tubes are deformed so that they are in sealing engagement with the wrappers of the respective cigarettes. Those annular sections of the tubes which move into actual contact with the wrappers of cigarettes are thinner than the remaining portions of the tubes and are bounded by convex internal and concave external surfaces.

20 Claims, 4 Drawing Figures

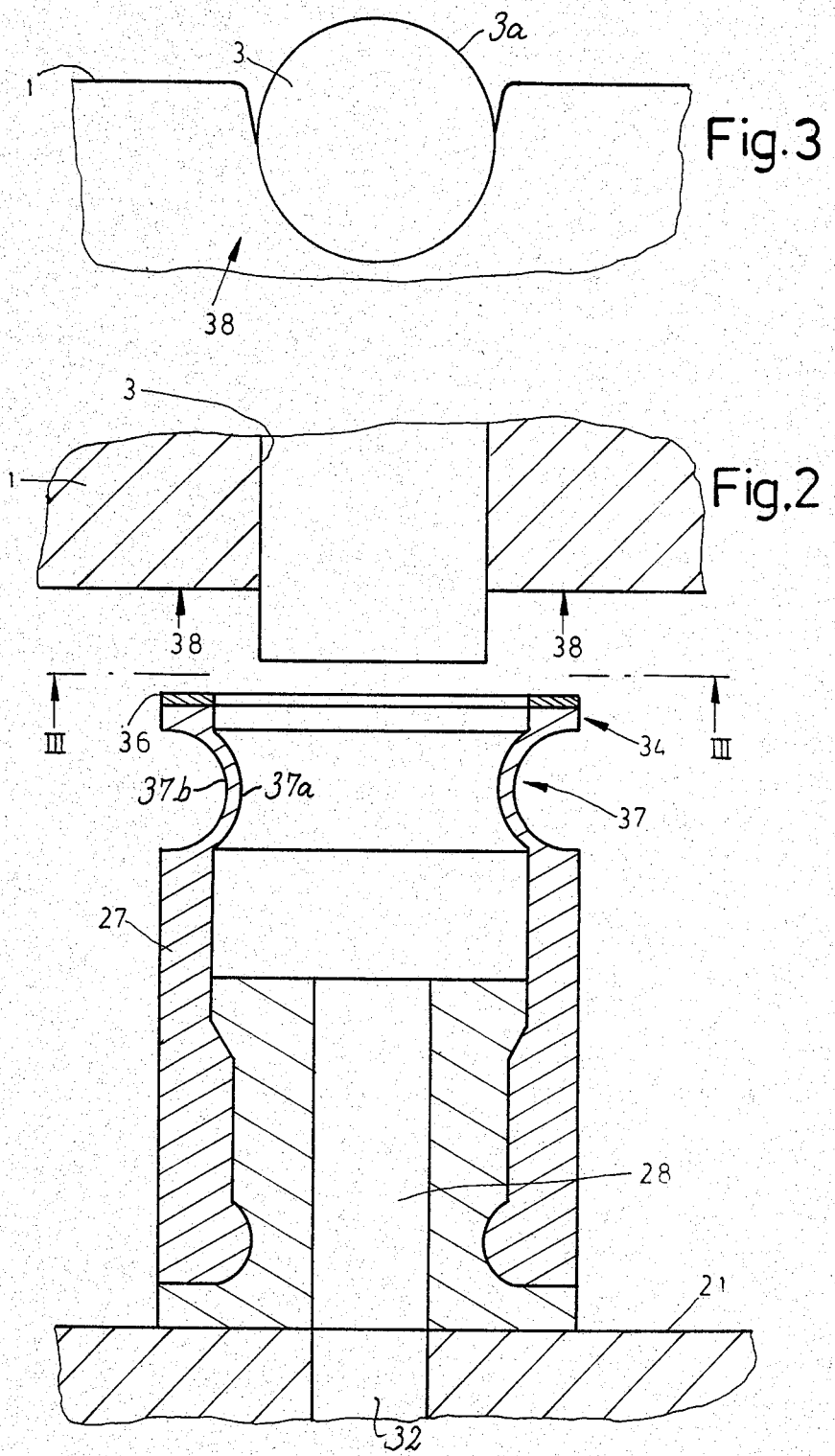

APPARATUS FOR TESTING CIGARETTES AND THE LIKE

CROSS-REFERENCE TO RELATED CASE

The apparatus of the present invention constitutes an improvement over and a further development of the apparatus which are disclosed in commonly owned U.S. Pat. No. 3,914,989 granted Oct. 28, 1975 to Joachim Reuland et al. for "Method and apparatus for testing cigarettes or the like" and in commonly owned U.S. Pat. No. 3,769,832 granted Nov. 6, 1973 to Anton Baier for "Apparatus for testing cigarettes or the like".

BACKGROUND OF THE INVENTION

The present invention relates to improvements in apparatus for testing cigarettes and analogous rod-shaped articles. More particularly, the invention relates to improvements in apparatus for testing the tubular wrappers of cigarettes or analogous rod-shaped articles (hereinafter called cigarettes or filter cigarettes for short) for the presence or absence of leaks including open seams, holes and frayed ends, for the condition of seals between the filter mouthpieces and tobacco-containing portions of filter cigarettes, for the extent of permeability of cigarette paper and/or for the extent of permeability of so-called ventilation or aerating zones including intentionally made holes provided in the wrappers of filter rod sections for admission of cool atmospheric air into the column of tobacco smoke. Still more particularly, the invention relates to improvements in cigarette testing apparatus of the type wherein a stream of testing air is admitted into one or both axial ends of a cigarette during travel through the testing station and while the respective end portion of the peripheral surface of the wrapper is sealingly engaged by an elastic sealing element.

Apparatus of the above outlined character are disclosed in the aforementioned U.S. Pats. Nos. 3,769,832 and 3,914,989. It is also known to install the sealing elements on rotary carriers which are mounted not unlike the wobble plates of certain types of pumps so that each sealing element moves toward the adjacent end portion of a cigarette to be tested during one half and moves away from such end portion during the other half of each revolution of the respective carrier. This ensures that the end portions of cigarettes are received in the adjacent sealing elements during admission of testing fluid into their fillers. The sealing elements consist of rubber or a similar elastomeric material and their inner diameters are variable so that they can be deformed into sealing engagement with the peripheral surfaces of wrappers forming part of cigarettes which are being transported toward and through the testing station.

Highly accurate testing of the wrappers for the permeability or the presence of leaks is particularly important when the filters of filter cigarettes are provided with aforementioned ventilation or aerating zones in order to admit predetermined quantities of air into the column of tobacco smoke. An important prerequisite for accurate testing is proper sealing of the end portions of the wrappers against entry of atmospheric air and/or against escape of testing fluid into the surrounding atmosphere. Even minor leaks at the ends of the wrappers are likely to greatly distort the results of measurements and can result in ejection of satisfactory cigarettes or in the failure to eject defective cigarettes.

In accordance with heretofore known proposals, elastically deformable sealing elements are moved into sealing engagement with the ends of cigarette wrappers by pneumatic deforming means or by resorting to reciprocable sleeves, plungers or analogous mechanical deforming elements. Such mode of deforming the elastic sealing elements is complex, expensive and not sufficiently reliable to ensure satisfactory testing of the wrappers which are formed with ventilation zones. It was further proposed to bias the end faces of cigarettes against sealing elements with a force which should suffice to prevent uncontrolled escape of testing fluid prior to penetration into the fillers of cigarettes (note, for example, FIGS. 7 and 8 of U.S. Pat. No. 3,914,989). Such mode of testing is highly likely to entail damage to (especially undesirable deformation of) the end portions of cigarettes.

OBJECTS AND SUMMARY OF THE INVENTION

An object of the invention is to provide a novel and improved apparatus which can test plain or filter cigarettes or analogous rod-shaped articles with a high degree of accuracy and gently so that the testing operation does not involve deformation of and/or other damage to the tested articles.

Another object of the invention is to provide an apparatus which can be used with advantage in existing filter tipping and other types of cigarette making and/or processing machines as a superior substitute for heretofore known testing apparatus.

A further object of the invention is to provide novel and improved sealing elements for use in the above outlined testing apparatus.

An additional object of the invention is to provide the apparatus with novel and improved means for reliably deforming the sealing elements into sealing engagement with the wrappers of rod-shaped articles not later than at the time when the articles receive one or more streams of testing fluid.

Still another object of the invention is to provide the testing apparatus with novel and improved means for ensuring predictable deformation of elastic sealing elements into engagement with the end portions of tubular wrappers forming part of plain or filter tipped cigarettes or other rod-shaped articles of the tobacco processing industry.

A further object of the invention is to provide a novel and improved method of testing the wrappers of cigarettes or the like for all kinds of defects including undersirable rate of air flow through the ventilating zones in the wrappers of filter mouthpieces forming part of filter cigarettes or the like.

An additional object of the invention is to provide a filter tipping machine which embodies the above outlined testing apparatus.

Still another object of the invention is to provide an apparatus which is simpler but more reliable than heretofore known apparatus and wherein the elastic sealing elements can stand long periods of continuous use.

The invention is embodied in an apparatus for testing the tubular wrappers of cigarettes or analogous rod-shaped articles each of which has a predetermined diameter. The apparatus comprises a conveyor having article at least one receiving means and a marginal portion adjacent to the receiving means, a carrier, at least one elastic tubular sealing element provided on the carrier and having an open end and an annular section adjacent to the open end and arranged to reduce its inner diameter from a value exceeding to a value less than the predetermined diameter in response to axial deformation of the sealing element, means for respectively moving the receiving means and the sealing element along first and second endless paths through the medium of the conveyor and carrier to thereby introduce the end portion of an article in the receiving means through the open end of and into the sealing element beyond the annular section during movement of the receiving means and carrier along first portions of the respective paths and to thereupon axially deform the sealing element by the marginal portion of the conveyor with attendant contraction of the annular section into sealing engagement with the wrapper of the introduced end portion during movement of the receiving means and sealing element along second portions of the respective paths, and means for admitting a gaseous testing fluid through the sealing element and into the sealingly engaged end portion of the article, either in the second portion or in a next-following third portion of the endless path of the sealing element.

The marginal portion of the conveyor is adjacent to an end portion of the receiving means and the latter is preferably arranged to receive articles in such a way that the one end portion of the article therein extends beyond the end portion of the receiving means as well as beyond the marginal portion of the conveyor.

The sealing element can be made of natural or synthetic rubber (the term "synthetic rubber" is intended to embrace all such substances which exhibit the required elasticity and can stand reasonable periods of use in the testing apparatus of a filter tipping machine or the like). In accordance with a presently preferred embodiment of the invention, the sealing element constitutes or resembles a hollow cylinder.

The conveyor can constitute or include a drum which is rotatable about a first axis and the carrier is preferably rotatable about a second axis which is inclined with reference to the first axis. The mounting of the carrier can resemble that of a wobble plate in an axial piston pump. The receiving means can include at least one axially parallel flute which is machined into or otherwise formed in the peripheral surface of the drum-shaped conveyor. The carrier is then adjacent to one end face of the drum-shaped conveyor and such end face is disposed in the region of the aforementioned marginal portion which can effect deformation of the sealing element during a certain stage of each revolution of the conveyor. The flute is recessed into the one end face of the conveyor, preferably to a depth which at least matches but preferably at least slightly exceeds the radius of an article.

The deformability of the annular section of the sealing element preferably exceeds the deformability of the remaining portion of the sealing element, and such remaining portion includes an annular end section which surrounds the open end of the sealing element and can constitute a ring-shaped bead. The bead is engaged by the marginal portion of the conveyor during movement of the sealing element along the second portion of its endless path. Greater deformability of the annular section of the sealing element can be achieved by reducing its wall thickness to less than the wall thickness of the remaining portion of the sealing element. In undeformed condition of the sealing element, its annular section is preferably formed with a convex internal surface and a concave external surface. The sealing element preferably further comprises reinforcing means which is disposed in the region of its open end, for example, on the end face of the aforementioned bead. The reinforcing means can comprise a metallic ring which is applied to the end face of the bead by vulcanizing, by resorting to an adhesive or in any other suitable way.

The novel features which are considered as characteristic of the invention are set forth in particular in the appended claims. The improved testing apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 2 is a greatly enlarged view of a detail in FIG. 1, with one of the tubular sealing elements about to receive one end portion of a cigarette;

FIG. 3 is a fragmentary end elevational view of the conveyor as seen in the direction of arrows from the line III—III of FIG. 2.

DESCRIPTION OF THE PREFERRED EMBODIMENTS

Figure 1:
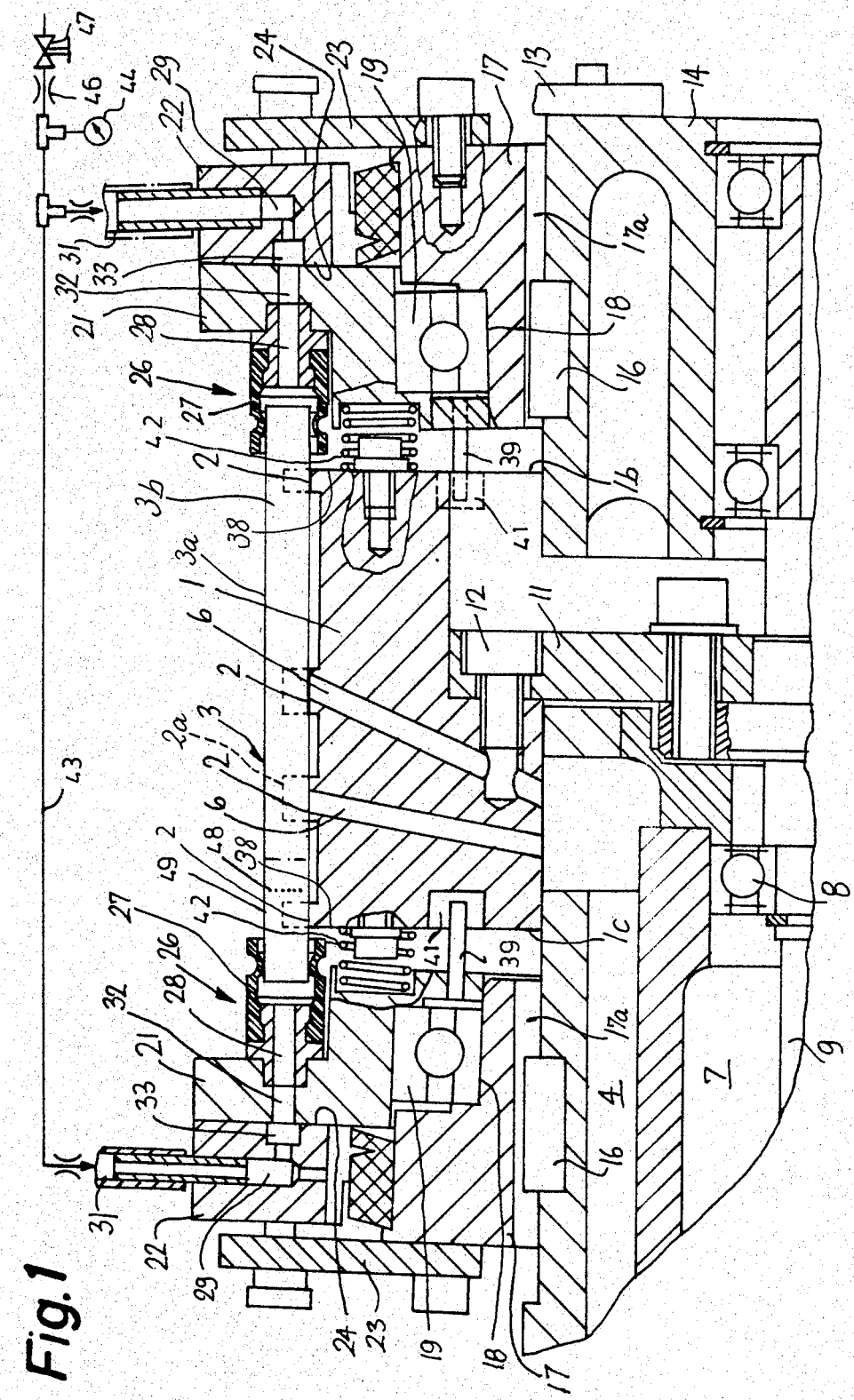
FIG. 1 is a fragmentary axial sectional view of an apparatus which embodies the invention.

Referring to FIG. 1, there is shown a cigarette testing apparatus which is similar to that disclosed in commonly owned U.S. Pat. No. 3,948,084 granted Apr. 6, 1976 to Bob Heitmann et al. The disclosure of this patent (as well as the disclosure of each other patent referred to in this specification) is incorporated herein by reference.

The apparatus comprises a rotary drum-shaped testing conveyor 1 which is rotatable about a horizontal axis and whose peripheral surface is formed with an annulus of axially parallel article receiving means 2 each including a composite flute composed of several aligned flutes machined into circumferentially extending ribs 2a of the conveyor 1. The conveyor 1 is installed in a filter tipping machine, e.g., a machine of the type known as MAX or MAX S (both manufactured and sold by the assignee of the present application) and is designed to receive, transport and release a succession of filter cigarettes 3 of unit length. A MAX machine is shown in FIG. 1 of the aforementioned U.S. Pat. No. 3,948,084. Each cigarette 3 has a tubular wrapper 3a including a first tubular component surrounding the tobacco-containing portion 3b of the cigarette and a second tubular component surrounding the filter plug 49 of the cigarette and being formed with a row of perforations 48 constituting the aforediscussed aerating or ventilating zone of the wrapper. Such ventilating zone is designed to permit entry of a predetermined quantity of cool atmospheric air into the column of tobacco smoke flowing into the smoker's mouth when the cigarette 3 is lighted. The purpose of testing is to ascertain the condition of the wrappers 3a of successive filter cigarettes 3, namely to detect the presence or absence of frayed ends, holes, open seams, the absence of adequate seals between the tobacco-containing portions and the filter plugs, excessive or insufficient permeability of the ventilating zones 48 and/or excessive or insufficient permeability of the remaining part of each wrapper 3a.

Each filter cigarette 3 is held in the respective receiving means 2 by suction in ports 6 which extend substantially radially of the body of the conveyor 1 and communicate with a channel 4 which is machined into or otherwise formed in a stationary hollow shaft 7. The intake end of the channel 4 is connected with a suction pump or another suitable suction generating device, not shown. The body of the conveyor 1 rotates on the stationary shaft 7 and the suction ports 6 leading to the flutes of a receiving means 2 are in communication with the channel 4 during that stage of each revolution of the conveyor 1 when such receiving means is to retain a cigarette 3 therein, namely during transport of such cigarette 3 from the conveyor which delivers untested cigarettes into successive receiving means 2 to a conveyor which receives successive tested cigarettes 3 from the conveyor 1. The depth of flutes which constitute the receiving means 2 at least equals but preferably at least slightly exceeds the radius of a cigarette 3. This is clearly shown in FIG. 3. Thus, the surface bounding a flute extends along a little more than half the periphery of the wrapper 3a of a cigarette 3 therein.

The means for rotating the conveyor 1 about the axis of the hollow shaft 7 comprises a drive shaft 9 which is journalled in bearings 8 in the interior of the shaft 7 and is connected to the body of the conveyor 1 by a ring-shaped coupling member 11 and screws 12. The drive shaft 9 is further rotatable in a stationary bearing sleeve 14 which is secured to the frame of the filter tipping machine by one or more links 13. Keys 16 are recessed into the peripheral surfaces of the shaft 7 and sleeve 14, and portions of such keys extend into axially parallel internal grooves 17a which are machined into hollow tubular supports 17 for antifriction ball bearings 19. The sleeve 14 may but need not be mounted on or connected with the stationary shaft 7. The axes of the bearings 19 are slightly inclined with reference to the axis of the conveyor 1 in opposite directions. These bearings are mirror symmetrical to one another with reference to a plane which is normal to the axis of the conveyor 1 and is disposed midway between the two bearings. The inner race of each bearing 19 surrrounds a slightly conical seat 18 of the respective support 17.

Each of the bearings 19 is surrounded by a ring-shaped carrier 21, and these carriers rotate in planes which are slightly inclined with reference to the aforementioned symmetry plane so that the carriers 21 are nearest to each other in the upper portion of FIG. 1 and are disposed at a maximum distance from one another at a level below the shaft 7. The outer sides of the carriers 21 are engaged by the sealing surfaces 24 of stationary valving elements 22 which are fixedly connected to the respective supports 17 by links 23. The carriers 21 can be shifted nearer to or further away from each other by moving the respective supports 17 along the corresponding keys 16; this renders it possible to convert the apparatus for the testing of shorter or longer cigarettes. Suitable clamping means (not specifically shown) are provided to releasably hold the supports 17 in selected positions with reference to the corresponding keys 16.

Each carrier 21 supports an annulus of equidistant combined sealing and fluid-admitting devices 26 of which only two are actually shown in FIG. 1. Each device 26 comprises a nipple 28 which is anchored in the respective carrier 21 and an elastic tubular sealing element 27. Each sealing element 27 on the left-hand carrier 21 is in substantial axial alignment with a sealing element 27 on the right-hand carrier 21. The outer end portion of each sealing element 27 is slipped onto the corresponding nipple 28 and is in sealing engagement therewith.

Each valving element 22 has a radially extending channel 29 for admission of a gaseous testing fluid (normally air) which flows radially inwardly from a supply conduit 43 and into an arcuate slot 33 machined into the sealing surface 24 of the respective valving element 22. The slots 33 are adjacent to the endless paths of annuli of axially parallel bores 32 which are machined into the respective carriers 21 and communicate with the axial bores of the corresponding nipples 28. The ends of the filler of a cigarette 3 receive compressed testing fluid while the corresponding nipples 28 travel along and their bores communicate with the respective arcuate slots 33. The length of the testing station (as considered in the circumferential direction of the conveyor 1) is determined by the length of the slots 33; such length is somewhat less than the distance between the neighboring bores 32 of the carriers 21 and somewhat less than the distance between two neighboring receiving means 2 at the periphery of the conveyor 1. The channels 29 of the valving elements 22 receive portions of nipples 31 which are sealingly secured to the conduit 43.

Each sealing element 27 is a hollow cylinder which is made of rubber or another elastomeric material and is preferably soft so as to allow for ready radial and/or axial deformation. As can be readily seen in FIGS. 2 and 4, the free end sections of the sealing elements 27 are open and are formed by ring-shaped beads 34 surrounding the respective open ends and adjacent to weakened annular sections 37 each of which has a convex internal surface 37a and a concave external surface 37b. The deformability or elasticity of the annular sections 37 is more pronounced than that of the respective beads 34 and/or any other parts of remaining portions of the respective sealing elements 27. In the embodiment which is actually shown in the drawing, such greater elasticity or deformability of the annular sections 37 is achieved by the simple expedient of making them thinner than the remaining portions of the sealing elements 27. This can be readily seen in FIGS. 2 and 4.

Figure 4:
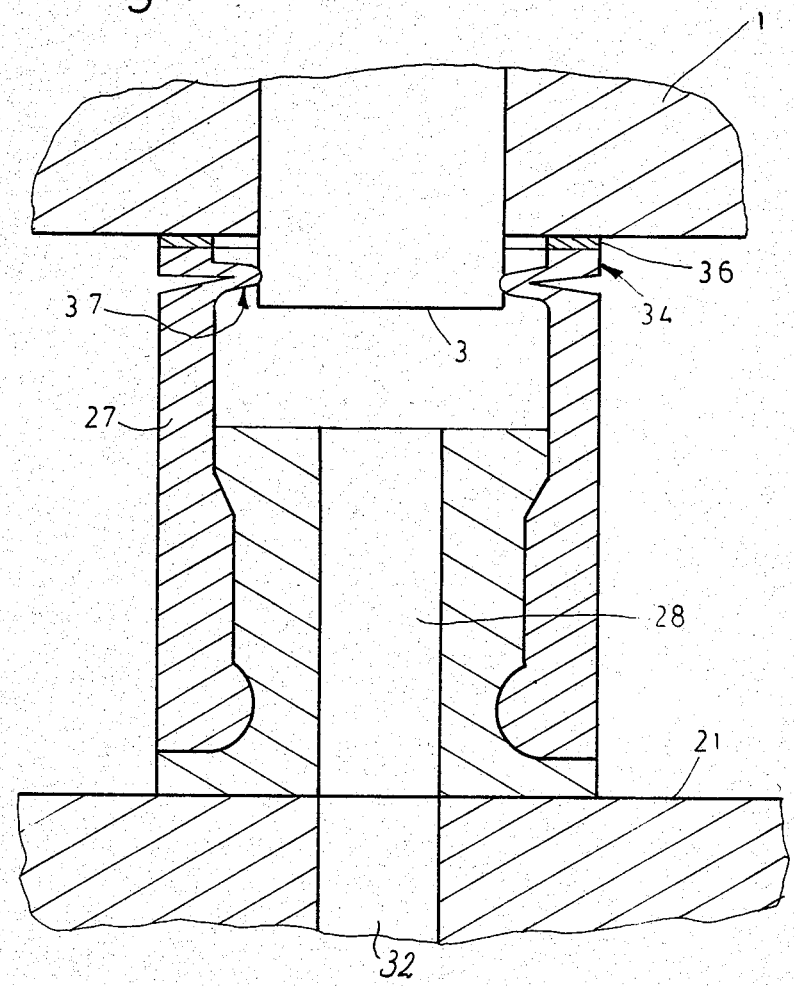
FIG. 4 is a view similar to that of FIG. 2 but showing the sealing element in axially deformed condition with its annular section in sealing engagement with the wrapper of the cigarette.

The beads 34 of the sealing elements 27 are reinforced or stiffened by metallic reinforcing rings 36 which are adhesively bonded or otherwise secured (e.g., vulcanized) to the end faces of the respective beads. Each reinforcing ring 36 can constitute a relatively thin layer or coat of a suitable metallic material and serves to reduce the deformability of the respective bead 34 to a value well below that of the annular section 37. FIG. 2 shows that the convex surface 37a of the tubular section 37 extends inwardly beyond the internal surface 27a of the adjacent portion of the sealing element 27 even when this sealing element is not deformed. The inner diameter of the annular section 37 in undeformed condition of the respective sealing element 27 at least slightly exceeds the diameter of a cigarette 3 which is to be tested. When the sealing element 27 is deformed axially in a manner as shown in FIG. 4, i.e., by applying pressure against the metallic reinforcing ring 36 in a direction toward the respective nipple 28, the tubular section 27 "buckles" and its inner diameter is reduced so that the convex internal surface 37a moves into sealing engagement with the peripheral surface of the wrapper 3a of a cigarette 3 whose end portion extends through the open end of and into the sealing element 27 through and beyond the annular section 37.

The conveyor 1 comprises two annular marginal portions 38 which constitute the means for effecting axial deformation of the respective sealing elements 27. FIG. 1 shows that the marginal portions include surfaces forming part of the respective end faces 1b, 1c of the conveyor 1 and surrounding the respective ends of the receiving means 2. Since the marginal portions 38 surround the major parts of the respective ends of the receiving means 2 (as shown in FIG. 3), they are evidently in a position to predictably deform the adjacent sealing elements 27 while such sealing elements approach, move past and advance beyond the respective arcuate slots 33 in the corresponding valving elements 22. The sealing elements 27 rotate with the respective carriers 21 which, in turn, rotate with the conveyor 1 but in mutually inclined planes as described above. The means for coupling the carriers 21 to the conveyor 1 comprises motion transmitting pins 39 which are anchored in the carriers 21 and extend into radially extending recesses 41 in the respective end faces 1b, 1c of the body of the conveyor 1 radially inwardly of the receiving means 2. The radially extending recesses 41 enable the carriers 21 to remain in their respective planes when the shaft 9 is driven by the main prime mover of the filter tipping machine and rotates the carriers as well as the conveyor 1. The testing apparatus further comprises coil springs 42 which are inserted between the conveyor 1 and the carriers 21 to ensure that successive sealing elements 27 invariably move away from the adjacent receiving means 2 of the conveyor 1 during movement of such sealing elements from the testing station (between the slots 33) toward the positions below the shaft 7. The springs 42 store energy while they travel toward the testing station and they dissipate energy during movement away from such station.

The conduit 41 is connected with a pressure gauge 44 and contains an adjustable flow restrictor 46 which determines the pressure of testing fluid flowing into the nipples 31. The conduit 43 further contains a suitable shutoff valve 47.

The mode of operation is as follows:

The shaft 9 is driven by the prime mover of the filter tipping machine or by any other suitable torque transmitting device. The coupling element 11 transmits torque from the shaft 9 to the body of the conveyor 1 and the latter transmits torque to the carriers 21 by way of the respective pins 39. The carriers 21 advance along endless paths whose planes are slightly inclined with reference to the path of movement of cigarettes 3 with the corresponding receiving means 2 of the conveyor 1. The RPM of the conveyor 1 is the same as that of the carriers 21. The aforementioned suction generating device draws air from the channel 4 of the hollow stationary shaft 7 and from those suction ports 6 which advance toward the testing station so that a freshly inserted cigarette 3 which is admitted into a receiving means 2 at a location remote from the testing station (namely, at a location where the corresponding portions of the rotating carriers 21 are disposed at a greater distance from one another to allow for unimpeded insertion of a cigarette into the corresponding receiving means) is attracted to the surfaces bounding the respective flutes and is held on the conveyor 1 during travel toward, past and beyond the testing station between the two arcuate slots 33.

As mentioned above, cigarettes 3 are inserted into the corresponding receiving means 2 at a location which is remote from the testing station, e.g., at a level below the conveyors 7 and 9 where the distance between the corresponding pair of aligned sealing elements 27 suffices to allow for unimpeded insertion of a cigarette 3 into the flutes between such sealing elements. This is shown in FIG. 2 where the illustrated end portion of the cigarette 3 is properly accommodated in the flutes of the respective receiving means 2 but its end face is still remote from the reinforcing ring 36 of the corresponding sealing element 27. The conveyor 1 and the carriers 21 continue to rotate and the sealing elements 27 move axially and nearer toward the respective end portions of the cigarette 3 therebetween. Not later than at the testing station, the end portions of the cigarette 3 not only enter the open ends of the respective sealing elements 27 but advance inwardly beyond the respective annular sections 37. Moreover, the marginal portions 38 of the conveyor 1 engage the reinforcing rings 36 of the respective sealing elements 27 and deform the sealing elements axially with attendant radial deformation of the corresponding annular sections 37 into sealing engagement with the peripheral surfaces of the respective end portions of the wrapper 3a. As explained above, the inner diameter of each annular section 37 in undeformed condition of the respective sealing element 27 at least slightly exceeds the diameter of a cigarette 3, and such inner diameter decreases in response to engagement of the respective marginal portion 38 with the reinforcing ring 36 with the result that the inner diameter of the annular section 37 decreases and the concave surface 37a sealingly engages the peripheral surface of the inserted end portion of the wrapper 3a. The just discussed sealing action is achieved not later than when the corresponding nipples 28 begin to receive testing fluid from the adjacent arcuate slots 33 whereby the pressure which is indicated by the gauge 44 denotes the condition of the tested article, i.e., the integrity or lack of integrity of the tubular wrapper 3a of such article. The mutual inclination of the axes of bearings 19 on the one hand and the axis of the conveyor 1 on the other hand suffices to ensure that the end portions of a cigarette 3 penetrate into the registering sealing elements 27 to an extent which suffices to enable the annular sections 37 to sealingly engage the corresponding end portions of the tubular wrapper 3a. The manner in which the axial length of a sealing element 27 is reduced by the corresponding marginal portion 38 of the conveyor 1 and in which the annular section 37 of such sealing element is deformed in response to axial deformation of the sealing element is shown in FIG. 4. Since the material of the annular section 37 is elastomeric, the section 37 can readily follow the outline of the peripheral surface of the wrapper 3a to ensure the establishment of a reliable seal during introduction of testing fluid into the respective end of the filler in the cigarette 3. Testing fluid can escape through the perforations 48 of the wrapper 3a, through the pores of paper or other wrapping material which is used to form the wrapper 3a, as well as through holes and/or open seams and/or gaps between the tobacco-containing portion and filter plug and/or frayed ends (if any). At any rate, the annular sections 37 of the sealing elements 27 prevent uncontrolled escape of testing fluid at the ends of the cigarette which advances through the testing station. In other words, any drop of pressure which is indicated by the gauge 44 or is detected by an automatic transducer (not shown) is indicative solely of the permeability of the aerating or ventilating zone, of the porosity of the material of the wrapper and/or of eventual defective portions of the tested wrapper 3a. The gauge 44 can be replaced with or used jointly with the aforementioned transducer which can transmit signals for ejection of defective cigarettes 3 from the conveyor 1 or from a next-following conveyor in the filter tipping machine. Reference may be had, for example, to commonly owned U.S. Pat. No. 3,914,989 granted Oct. 28, 1975 to Joachim Reuland et al. for "Method and apparatus for testing cigarettes or the like."

When a cigarette 3 advances beyond the testing station between the slots 33, the corresponding sealing elements 27 move away from the respective end portions of such cigarette with attendant disengagement of the annular sections 37 from the peripheral surface of the wrapper 3a. The cigarette is removed from the corresponding receiving means 2 when such removal cannot be interfered with by the sealing elements 27. Gradual termination of radial deformation of annular sections 37 is attributable to the fact that the axial deformation of sealing elements 27 is gradually reduced as the corresponding portions of the carriers 21 continue to rotate with but move substantially axially of and away from the respective marginal portions 38.

Suction in the ports 6 for a receiving means 2 is cut off at the locus where a freshly tested cigarette 3 is about to leave the conveyor 1. Segregation of defective cigarettes 3 from satisfactory cigarettes can take place on the conveyor 1 or on one of the conveyors which follow the conveyor 1 and on which the cigarettes can be subjected to one or more additional tests, e.g., to ascertain the density of their tobacco fillers and/or to ascertain the density of their tobacco-containing ends.

An important advantage of the improved apparatus is its surprising simplicity. Thus, the conveyor 1 can serve as a means for transporting cigarettes 3 seriatim toward, past and beyond the testing station and also as a means for effecting axial deformation of successive pairs of aligned sealing elements 27 with attendant establishment of sealing action between the annular sections 37 of such sealing elements and the peripheral surfaces of the corresponding wrappers 3a. All that is necessary is to incline the endless paths of movement of successive sealing elements 27 with reference to the endless path of movement of receiving means 2 in such a way that the cigarettes 3 can be readily inserted into the respective receiving means 2 while the receiving means are remote from the testing station, that the end portions of the cigarettes gradually penetrate into the open ends and inwardly beyond the annular sections 37 of the respective sealing elements 27 in first portions of the respective endless paths (for the sealing elements 27 and receiving means 2), and that the marginal portions 38 of the conveyor effect axial deformation of sealing elements 27 and attendant radial deformation of the annular sections 37 not later than on arrival of such sealing elements at the testing station, i.e., in predetermined second portions of the endless paths of the sealing elements 27 and receiving means 2.

Uncontrollable deformation of sealing elements 27 is prevented by the simple expedient of designing the marginal portions 38 of the conveyor 1 in such a way that their surfaces (portions of the respective end faces 1b, 1c of the conveyor 1) surround more than one-half of each cigarette 3 which is properly confined and held in the respective receiving means. This ensures predictable axial shifting of the reinforcing rings 36 even when the conveyor 1 is rotated at a very high speed such as is necessary in a modern filter tipping machine receiving the output of one or more modern high-speed cigarette rod making machines which are capable of turning out in excess of 8000 cigarettes per minute. As explained above, the depth of the receiving means 2, as considered in the radial direction of the conveyor 1, at least equals but preferably exceeds the radius of a cigarette 3.

The provision of beads 34 and reinforcing rings 36 on the sealing elements 27 also contributes to predictable axial deformation of the sealing elements and to equally predictable radial deformation of their annular sections 37. Instead of using sealing elements wherein the elasticity of annular sections 37 is enhanced by reducing the wall thicknesses of the corresponding portions of sealing elements, it is also possible to assemble each sealing element from two relatively stiff sections (one of which is slipped onto the corresponding nipple 28 and the other of which replaces or constitutes the corresponding bead 34 and its reinforcing ring 36) and from a softer or more elastic section which is installed between and vulcanized or otherwise bonded to the two stiffer sections to constitute a functional equivalent of the annular section 37.

The feature that the annular sections 37 have convex internal surfaces 37a contributes to more reliable sealing action of such sections as well as to more predictable radial deformability of each annular section in response to axial deformation of the respective sealing element. The same holds true for the provision of concave external surfaces 37b. Moreover, such configuration of the annular sections 37 (i.e., that each thereof has a convex internal surface and a concave external surface even when the corresponding sealing element 27 is not subjected to axial deforming stresses) ensures that the concave surfaces 37a can sealingly engage the peripheral surfaces of the wrappers 3a in response to surprisingly short axial deformation of the sealing elements.

An important advantage of the improved testing apparatus is that the means for effecting radially inward deformation of annular sections 37 in predetermined portions of the endless paths of the respective sealing elements 27 can be achieved without resort to plungers, air blowing nozzles, sleeves or other additional parts which would contribute to the bulk, cost and sensitivity of the apparatus. Instead, the conveyor 1 is designed in such a way that it can effect axial deformation of sealing elements 27 in good time before the respective cigarettes 3 reach the testing station and that it allows the sealing elements 27 to reassume their normal shapes in good time prior to arrival at the article-discharging station. Moreover, the sealing action of annular sections 37 is highly satisfactory, not only when the wrappers 3a are perfect cylinders but also when the shape of such wrappers deviates appreciably from a circular shape. Still further, the sealing action is established and terminated automatically, invariably at an optimum time (when the respective cigarette enters or is about to enter the testing station) and is maintained for the requisite interval of time to ensure adequate sealing while the end portions of the cigarette receive testing fluid. The absence of discrete deforming means for each sealing element 27 is of particular importance in modern high-speed testing apparatus which must test the articles at a very high frequency so that the provision of reciprocatory or otherwise movable parts for the express purpose of deforming the corresponding sealing elements for a few milliseconds during each revolution of the conveyor would result in highly pronounced wear and would necessitate frequent stoppages for inspection and/or repair. In the improved apparatus, the wear upon the reinforcing rings 36 of sealing elements 27 and on the surfaces of marginal portions 38 of the conveyor 1 is negligible since they move into and from engagement with one another without any slippage or with negligible slippage.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. In an apparatus for testing the tubular wrappers of cigarettes or analogous rod-shaped articles having predetermined diameters, a conveyor having at least one article receiving means and also having a marginal portion adjacent to said receiving means; at least one carrier; at least one elastic tubular sealing element provided on said carrier and having an open end and an annular section adjacent to said open end and arranged to reduce the sealing element's inner diameter at said annular section from a value exceeding to a value less than said predetermined diameter in response to axial deformation of the sealing element; means for respectively moving said receiving means and said sealing element along first and second endless paths by way of said conveyor and said carrier so as to thereby introduce one end portion of an article in said receiving means through the open end of and into said sealing element beyond said annular section during movement of said receiving means and said sealing element along first portions of the respective paths and to thereupon axially deform said sealing element by deforming contact of the sealing element with said marginal portion with attendant contraction of said annular section into sealing engagement with the wrapper of the introduced end portion during movement of said receiving means and said sealing element along second portions of the respective paths; and means for admitting a gaseous testing fluid through said sealing element and into the sealingly engaged end portion of the article, while the other end portion of the article is sealed from the surrounding atmosphere.

2. The structure of claim 1, wherein said receiving means has an end portion and said marginal portion is adjacent to the end portion of said receiving means, the latter being arranged to receive articles in such a way that the one end portion of the article therein extends beyond the end portion of the receiving means as well as beyond said marginal portion.

3. The structure of claim 1, wherein said sealing element consists of natural or synthetic rubber.

4. The structure of claim 1, wherein said sealing element is a hollow cylinder.

5. The structure of claim 1, wherein said conveyor is rotatable about a first axis and said carrier is rotatable about a second axis which is inclined with reference to said first axis.

6. The structure of claim 5, wherein said conveyor includes a drum having a peripheral surface and an axially parallel flute provided in said peripheral surface and forming part of or constituting said receiving means.

7. The structure of claim 6, wherein said drum has an end face in the region of said marginal portion and said carrier is adjacent to said end face.

8. The structure of claim 1, wherein said marginal portion has an end face and said receiving means is recessed into said end face and has a depth at least matching the radius of an article.

9. The structure of claim 8, wherein said conveyor includes a drum having two end faces one of which is the end face of said marginal portion, said drum further having a peripheral surface and said receiving means constituting or including an axially parallel flute in said peripheral surface.

10. The structure of claim 1, wherein the deformability of said annular section exceeds the deformability of the remaining portion of said sealing element.

11. The structure of claim 10, wherein said remaining portion of said sealing element includes an annular end section surrounding said open end and being engageable by said marginal portion during movement of said sealing element along the second portion of the respective path.

12. The structure of claim 11, wherein said end section is a ring-shaped bead of said sealing element.

13. The structure of claim 10, wherein the wall thickness of said annular section is less than the wall thickness of said remaining portion of said sealing element.

14. The structure of claim 1, wherein the inner diameter of said annular section in undeformed condition of said sealing element is less than the diameter of said open end.

15. The structure of claim 14, wherein said annular section has a convex internal surface.

16. The structure of claim 14, wherein said annular section has a concave external surface.

17. The structure of claim 1, further comprising means for reinforcing said sealing element in the region of said open end.

18. The structure of claim 17, wherein said sealing element has a ring-shaped bead surrounding said open end and said reinforcing means is provided on said bead.

19. The structure of claim 18, wherein said bead has an end face and said reinforcing means is provided on the end face of said bead.

20. The structure of claim 17, wherein said reinforcing means comprises a metallic ring.

* * * * *